United States Patent [19]
Huth et al.

[11] Patent Number: 5,350,750
[45] Date of Patent: Sep. 27, 1994

[54] β-CARBOLINE-3-HYDROXYALKYLCAR-BOXYLIC ACID ESTER DERIVATIVES, PROCESS FOR THEIR PRODUCTION AND THEIR USE IN PHARMACEUTICAL AGENTS

[75] Inventors: Andreas Huth; Martin Krüger; Dieter Seidelmann; Ralph Schmiechen; Werner Krause; Herbert Schneider; Lechoslaw Turski, all of Berlin, Fed. Rep. of Germany

[73] Assignee: Schering Aktiengesellschaft, Berlin und Bergkamen, Fed. Rep. of Germany

[21] Appl. No.: 977,405

[22] PCT Filed: Apr. 15, 1991

[86] PCT No.: PCT/DE92/00314
§ 371 Date: Mar. 1, 1993
§ 102(e) Date: Mar. 1, 1993

[87] PCT Pub. No.: WO92/19619
PCT Pub. Date: Nov. 12, 1992

[30] Foreign Application Priority Data

Apr. 27, 1991 [DE] Fed. Rep. of Germany ....... 4114397

[51] Int. Cl.$^5$ .................. A61K 31/53; A61K 31/495; A61K 31/50; A61K 31/44; C07D 401/00; C07D 471/02
[52] U.S. Cl. .................. 514/253; 514/241; 514/249; 514/269; 514/274; 514/292; 544/219; 544/238; 544/298; 544/310; 544/315; 544/318; 544/329; 544/353; 544/354; 544/361; 544/229; 546/14; 546/85; 546/86
[58] Field of Search .................. 546/85, 86, 14; 514/292, 241, 253, 269, 249, 274; 544/219, 238, 298, 310, 315, 318, 229, 405, 353, 354, 361

[56] References Cited

U.S. PATENT DOCUMENTS

| | | | |
|---|---|---|---|
| 4,371,536 | 2/1983 | Braestrup et al. | 546/86 |
| 4,435,403 | 3/1984 | Braestrup et al. | 546/86 |
| 4,596,808 | 6/1986 | Braestrup et al. | 546/86 |
| 4,731,358 | 3/1988 | Huth et al. | 546/86 |
| 4,877,792 | 10/1989 | Biere et al. | 546/86 |
| 4,894,377 | 1/1990 | Seidelmann et al. | 546/86 |
| 4,945,090 | 7/1990 | Schmiechen et al. | 546/86 |
| 4,960,777 | 10/1990 | Biere et al. | 546/86 |
| 5,010,077 | 4/1991 | Braestrup et al. | 546/86 |

FOREIGN PATENT DOCUMENTS

| | | |
|---|---|---|
| 30254 | 6/1982 | European Pat. Off. . |
| 54507 | 6/1982 | European Pat. Off. . |
| 110814 | 6/1984 | European Pat. Off. . |
| 130140 | 1/1985 | European Pat. Off. . |
| 3540654 | 5/1987 | Fed. Rep. of Germany . |

OTHER PUBLICATIONS

Organic Chemistry, 3rd Edition, Solomons (1984) pp. 281, 675–676 and 794.

Primary Examiner—Cecilia Tsang
Attorney, Agent, or Firm—Millen, White, Zelano & Branigan

[57] ABSTRACT

β-carboline-3-hydroxyalkylcarboxylic acid ester derivatives of formula I

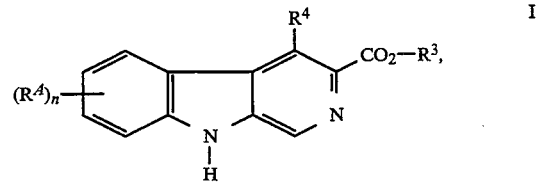

in which $R^A$, n, $R^4$ and $R^3$, have the meaning indicated in the claims, as well as their production and their use in pharmaceutical agents are described.

6 Claims, No Drawings

β-CARBOLINE-3-HYDROXYALKYLCARBOXYLIC ACID ESTER DERIVATIVES, PROCESS FOR THEIR PRODUCTION AND THEIR USE IN PHARMACEUTICAL AGENTS

BACKGROUND OF THE INVENTION

The invention relates to new β-carboline-3-hydroxyalkylcarboxylic acid ester derivatives, their production and use in pharmaceutical agents.

From numerous publications, such as, for example, from EP-A-54 507, it is known that β-carbolines have an affect on the central nervous system and are used as psychopharmaceutical agents.

The compounds substituted according to the invention have a good affinity for the benzodiazepine receptors. For use as pharmaceutical agents it is possibly advantageous if the substances are eliminated more quickly and thus have a shorter duration of action in comparison with other β-carbolines. Such cases exist, for example, in the use as soporific or in patients with a slow metabolism (older patients). Because of the hydroxyl group already present and important for the conjugation and elimination, a shorter duration of action of the compounds according to the invention exists.

SUMMARY OF THE INVENTION

The compounds according to the invention have general formula I

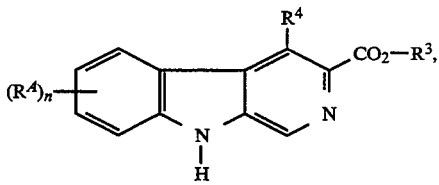

in which
$R^4$ means halogen, $-CHR^1-R^2$ or $OR^5$ and n is 1 or 2 and
$R^1$ means hydrogen or $C_{1-4}$-alkyl
$R^2$ means hydrogen, $C_{1-4}$-alkyl, $O-C_{1-4}$-alkyl or an optionally substituted phenyl, benzyl or phenoxy radical and
$R^5$ represents hydrogen, $C_{1-4}$-alkyl, $C_{3-7}$-cycloalkyl or an optionally substituted phenyl, benzyl or hetaryl radical
$R^4$ means hydrogen, $C_{1-4}$-alkyl or $C_{1-4}$-alkoxy-$C_{1-2}$-alkyl and
$R^3$ means a straight-chain or branched $C_{1-6}$-alkyl, that is substituted once to four times with $OR^6$ and
$R^6$ means hydrogen, $C_{1-4}$-alkyl or a hydroxy protective group as well as their isomers and acid addition salts.

Substituent $R^4$ can be in the A ring in position 5-8, preferably in 5, 6 or 7 position.

The alkyl groups may be both straight chain and branched chain radicals such as, for example, methyl, ethyl, propyl, isopropyl, butyl, isobutyl, sec. butyl, tert. butyl, pentyl, isopentyl and hexyl.

By halogen is meant fluorine, chlorine, bromine and iodine respectively.

Cycloalkyl respectively stands for cyclopropyl, cyclobutyl, cyclopentyl, cyclohexyl, cycloheptyl.

If $R^5$ means a hetaryl radical, then it is 5- or 6-membered and contains 1-3 heteroatoms such as nitrogen, oxygen and/or sulfur. For example, the following 5- and 6-ring heteroaromatic compounds can be mentioned: pyridine, pyrimidine, pyrazine, pyridazine, triazine, furan, thiophene, pyrrole, thiazole, imidazole. The hetaryl radical can have a condensed benzene radical such as quinoline, isoquinoline, quinoxaline.

The phenyl, benzyl and hetaryl radical $R^5$ can be substituted once to three times in any position. Suitable substituents are halogen, nitro, cyano, $C_{1-4}$-alkyl, $C_{1-4}$-alkoxy, trifluoromethyl, $SO_2-C_{1-4}$-alkyl, amino and $C_{1-4}$-alkoxycarbonyl, and halogens such as fluorine, chlorine and bromine are preferred.

Nitrogen-containing heterocycles optionally substituted with halogen or $C_{1-4}$-alkyl can be considered as preferred hetaryl radicals $R^5$.

As the substituents of phenyl, benzyl and phenoxy radical $R^2$, the substituents of the aromatic compounds mentioned for $R^5$ are suitable, especially halogen such as chlorine and bromine.

If $R^6$ means a hydroxy protective group, then all protective groups usually used that are not attacked under the reaction conditions are suitable. Examples of such protective groups are cyclic ethers such as tetrahydropyranyl, tetrahydrofuranyl, benzyl, substituted benzyl such as p-methoxybenzyl, 4-methylbenzyl, trityl, allyl, trialkylsilyl such as trimethylsilyl, t-butyldimethylsilyl, that are obtained by reaction of the hydroxy group, for example, with dihydropyran, 2-chlorotetrahydrofuran, benzylhalide, allylhalide or trimethylsilylhalide. If substituent $R^6$ contains several hydroxy groups, then cyclic acetals or ketals can be present, such as 1,3-dioxane or 1,3-dioxolane radicals such as 2-phenyl-1,3-dioxane, 2,2-dimethyl-1,3-dioxolane, that are produced for example by reaction with acetone, an enolether, 1,1-alkyl dihalide or acetone dimethyl ketal.

If the chiral centers are present, compounds of formula I can be present in the form of stereoisomers and their mixtures.

The physiologically compatible acid addition salts are derived from the known inorganic and organic acids such as, for example, hydrochloric acid, hydrobromic acid, sulfuric acid, phosphoric acid, formic acid, acetic acid, benzoic acid, maleic acid, fumaric acid, succinic acid, tartaric acid, citric acid, oxalic acid, glyoxylic acid as well as from alkanesulfonic acids such as, for example, methanesulfonic acid, ethanesulfonic acid, benzenesulfonic acid, p-toluenesulfonic acid, among others.

The compounds of formula I as well as their acid addition salts are usable as pharmaceutical agents because of their affinity to benzodiazepine receptors and have an antagonistic, inverse agonistic and agonistic effect on the known properties of the benzodiazepines.

At the same time, the compounds according to the invention show a shorter duration of action in comparison with other β-carbolines and are suitable as soporifics and as psychopharmaceutical agents, especially as anxiolytic agents. Further they show memory-promoting properties.

For use of the compounds according to the invention as pharmaceutical agents they are put in the form of pharmaceutical preparation, that, besides the active ingredient for enteral or parenteral administration, contain suitable pharmaceutical, organic or inorganic inert vehicles such as, for example, water, gelatin, gum arabic, lactose, starch, magnesium stearate, talc, vegetable oils, polyalkyleneglycols, etc. The pharmaceutical preparations can be available in solid form, for example, as tablets, coated tablets, suppositories, capsules or in liquid form, for example, as solutions, suspensions or emulsions. Moreover, optionally, they contain auxiliary agents such as preservatives, stabilizers, wetting agents or emulsifiers, salts for changing of the osmotic pressure or buffers.

Especially suitable for parenteral use are injection solutions or suspensions, especially aqueous solutions of the active compounds in polyhydroxy-ethoxylated caster oil.

As vehicle systems surface-active auxiliary agents such as salts of bile acids or animal or vegetable phospholipids, but also mixtures of them as well as liposomes or their components can be used.

For the oral use tablets, coated tablets or capsules with talc and/or hydrocarbon vehicles or binders, such as, for example, lactose, corn or potato starch, are especially suitable. The use can even take place in liquid form, such as, for example, as juice to which a sweetener is optionally added.

The compounds according to the invention are introduced in a dosage unit of 0.05 to 100 mg of active substance in a physiologically compatible vehicle.

The compounds according to the invention are generally used in a dose of 0.1 to 300 mg/day, preferably 0.1 to 30 mg/day, analogously to diazepam.

The production of compounds according to the invention takes place according to methods known in the art. For example, compounds of formula I are achieved in that a) compounds of formula II

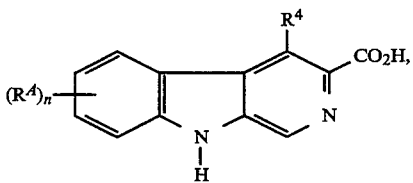

in which
$R^4$, n and $R^4$ have the above meaning, are reacted with epoxides of formula III

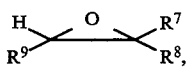

in which $R^7$, $R^8$ and $R^9$ each are hydrogen or $C_{1-4}$-alkyl, to prepare compounds of formula I with $R^3$ in the meaning of a straight-chain or branched $C_{2-6}$-alkyl group, that is substituted with hydroxy or b) compounds of formula IV

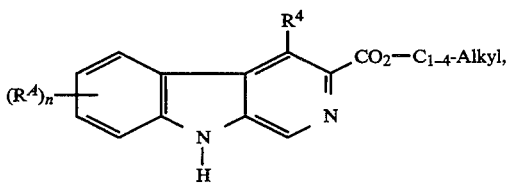

in which $R^4$, n and $R^4$ have the above meaning are transesterified and optionally then substituent $R^5$ is transetherified or hydroxy protective group $R^6$ is cleaved off or the isomers separated or the acid addition salts are formed.

The reaction of β-carboline-3-carboxylic acids of formula II with epoxides takes place at an elevated temperature, preferably from 50° to 150° C. in dipolar aprotic solvents, such as dimethylformamide, dimethylsulfoxide or ethers such as dioxane, ethyleneglycoldimethyl ether in the presence of acids. As acids, organic, inorganic and Lewis acids such as formic acid, acetic acid, propionic acid, hydrochloric acid, sulfuric acid or aluminumtrichloride are suitable.

The transesterification takes place according to process variant b) for the introduction of substituted alkyl radicals, for example, by reacting the alcohol, that contains a free or protected hydroxy group, at elevated temperature, preferably up to boiling temperature of the reaction mixture in the presence of titaniumtetraisopropylate. The reaction can be performed in the corresponding alcohol as solvent or by addition of an inert solvent such as xylene, toluene or N-methyl-pyrrolidone and is completed after one to five hours (Synth. 1982, 826; Synth. 1982, 138).

The optionally following modification of ether radical $R^5$ takes place according to methods described in EP-A-130 140 for cleaving the benzyl radical and etherification with a reactive derivative $R^5X$, in which X means halogen, tosylate, mesylate or triflate, in the presence of a base in a polar solvent, as described, for example, in EP-A-234 173 and EP-A-237 467. A suitable method for cleaving the benzyl group is, e.g., also the hydrogenolytic cleavage with palladium hydroxide as catalyst in the presence of cyclohexane, that is performed in protic solvents such as alcohols at elevated temperature preferably from 50 to 150° C.

Protective group $R^6$ of the hydroxy group can be removed depending on the type of protective group. If it is cleaved under acid conditions, then mineral acids and organic acids and their mixtures are suitable such as, for example, formic acid, acetic acid, trifluoroacetic acid, hydrochloric acid, sulfuric acid, among others, or Lewis acids such as boron trifluoride etherate. Silyl protective groups can be removed for example with fluorides such as tetrabutylammonium fluoride or cesium fluoride.

The isomeric mixtures can be separated into the diastereomers or enantiomers according to usual methods such as, for example, crystallization, chromatography or salt formation.

For the formation of the physiologically compatible acid addition salts, a compound of formula I is dissolved, e.g., in a little alcohol and mixed with a concentrated solution of the desired acid.

If the production of initial compounds is not described, they are known or are producible analogously to known compounds or processes described here.

For example, the production of 3-carboxylic acid esters of formula IV is described in EP-A 54 507, EP-A 237 467, EP-A-234 173, EP-A-130 140, EP-A-137 390 and EP-A-222 693. The production of β-carboline-3-carboxylic acids takes place for example according to the processes described in EP-A-161 574 or by usual acid or alkaline hydrolysis of the esters.

The following examples are to explain the process according to the invention.

EXAMPLE 1

3.62 g of 6-benzyloxy-4-methoxymethyl-β-carboline-3-carboxylic acid in 40 ml of dimethylformamide, 0.57 ml of glacial acetic acid and 7.21 of isobutylene oxide is stirred for 3 hours at 80° C. After addition of another 3.6 g of isobutylene oxide it is stirred 5 hours more at 80° C. After addition of 0.57 ml of glacial acetic acid and 7.21 of isobutylene oxide it is stirred 8 hours more at 80° C. The dimethylformamide is distilled off, the residue mixed with water and after setting the pH to 4-5 extracted with ethyl acetate. After concentration by evaporation the product is purified by column chromatography and recrystallized from ethyl acetate. 2.33 g (53.6% of theory) of 6-benzyloxy-4-methoxymethyl-β-carboline-3-carboxylic acid-(2-hydroxy-2-methyl)-propyl ester of a melting point of 163–165° C. is obtained.

EXAMPLE 2

2.17 g of 6-benzyloxy-4-methoxymethyl-β-carboline-3-carboxylic acid-(hydroxy-2-methyl)-propyl ester in 40 ml of ethanol and 20 ml of cyclohexane is mixed under nitrogen with 220 mg of Pd(OH)$_2$ and stirred for 1 hour at 110° C. It is filtered and concentrated by evaporation. The product is purified by column chromatography and recrystallized from hexane/ether. 1.67 g (97.1% of theory) of 6-hydroxy-4-methoxymethyl-β-carboline-3carboxylic acid-(2-hydroxy-2-methyl)-propyl ester of a melting point of 196° C. is obtained.

EXAMPLE 3

0.36 g of KOH is dissolved in 10 ml of DMSO and mixed with 1.72 g of 6-hydroxy-4-methoxymethyl-β-carboline-3-carboxylic acid-(2-hydroxy-2-methyl)-propyl ester. 0.69 g of chloropyrazine in 3 ml of DMSO is added and stirred for 4.5 hours at 90° C. After cooling it is poured in ice water, acidified with acetic acid to pH 5 and extracted with ethyl acetate. The product is purified by column chromatography and recrystallized on ethyl acetate. 0.688 g (32% of theory) of 4-methoxymethyl-6-(2-pyrazinyloxy)-β-carboline-3-carboxylic acid-(2-hydroxy-2-methyl)propyl ester of a melting point of 151° C. is obtained.

EXAMPLE 4

0.856 g of 6-(5-bromo-2-pyridyloxy)-4-methoxymethyl-β-carboline-3-carboxylic acid is introduced in 20 ml of dimethylformamide and mixed with 0.114 ml of glacial acetic acid and 1.8 ml of isobutylene oxide. Then it is stirred for 3 hours at 80° C. 0.9 ml of isobutylene oxide in 8 ml of dimethylformamide is added and stirred for 4 hours at 80° C. After addition of 0.114 ml of glacial acetic acid and 1.8 ml of isobutylene oxide in dimethylformamide it is stirred for 12 hours at 80° C. The solvent is distilled off, the residue is taken up in ethyl acetate and water and filtered. The organic phase of the filtrate is concentrated by evaporation and purified by column chromatography. After recrystallization from ethyl acetate, 0.251 g (25.1% of theory) of 6-(5-bromo-2-pyridyloxy)-4-methoxymethyl-β-carboline-3-carboxylic acid-(2-hydroxy-2-methyl)propyl ester of a melting point of 176° C. is obtained.

EXAMPLE 5

404 mg of 6-benzyloxy-4-methoxymethyl-β-carboline-3-carboxylic acid isopropyl ester is suspended in a mixture of 3 ml of glycol and 3 ml of xylene, mixed with 0.07 ml of titaniumisopropylate and stirred for 5 hours at 140° C. The solvent and the excess glycol are distilled off on the bulb tube and the residue is purified by column chromatography (toluene: glacial acetic acid: water 10:10:1). 230 mg of 6-benzyloxy-4-methoxymethyl-β-carboline-3-carboxylic acid- (2-hydroxy)-ethyl ester of a melting point of 190°–192° C. is obtained.

In a analogous way, there are produced:

6-Benzyloxy-4-methoxymethyl-β-carboline-3-carboxylic acid-(3-hydroxypropyl)-ester, melting point 165°–167° C.

5-Isopropoxy-4-methyl-β-carboline-3-carboxylic acid-(2,3-dihydroxyprop-1-yl)-ester, melting point 146°–150° C.

6-Benzyloxy-4-methoxymethyl-β-carboline-3-carboxylic acid-(2,2-dimethyl-1,3-dioxolan-4-yl-methyl)-ester, melting point 135°–138° C.

6-Benzyloxy-4-methoxymethyl-β-carboline-3-carboxylic acid-(2-phenyl-1,3-dioxan-5-yl)-ester, melting point 218°–220° C.

6-Benzyloxy-4-methoxymethyl-β-carboline-3-carboxylic acid-(2-hydroxyethyl)-ester, melting point 230°–235° C.

6-Benzyloxy-4-methoxymethyl-β-carboline-3-carboxylic acid-(2-hydroxy-propyl)-ester in a mixture with (2-hydroxy-1-methyl-ethyl)-ester in a ratio of 65:35. The pure isomers are obtained by crystallization from acetonitrile.

5-(4-Chlorophenoxy)-4-methoxy-β-carboline-3-carboxylic acid-(2-hydroxyethyl)-ester, melting point 159°–161° C.

5-(4-Chlorophenoxy)-4-methoxy-β-carboline-3-carboxylic acid-(2-methoxy-1-methylethyl)-ester, melting point 151°–153° C.

5- (4-Chlorophenoxy)-4-methoxy-β-carboline-3-carboxylic acid-(2-methoxyethyl)-ester, melting point 168°–168° C.

5-(4-Chlorophenoxy)-4-methoxy-β-carboline-3-carboxylic acid-(2-hydroxypropyl)-ester, melting point 121°–124° C. in a mixture with (2-hydroxy-1-methyl-ethyl)-ester in a ratio of 60:40. The pure ester is obtained by crystallization from acetonitrile, melting point 164°–166° C. and melting point 177°–180° C.

Threo-6-benzyloxy-4-methoxymethyl-β-carboline- 3-carboxylic acid-(3-hydroxy-1-methyl-propyl)-ester, melting point 87°–90° C.

Erythro-6-benzyloxy-4-methoxymethyl-β-carboline-3-carboxylic acid-(3-hydroxy-1-methyl-propyl)-ester, melting point 121°–126° C.

6-(5-Bromopyrid-2-yl)-oxy-4-methoxymethyl-β-carboline-3-carboxylic acid-(2-hydroxy-2-methyl)-propyl ester, melting point 176° C.

6-Benzyloxy-4-methoxymethyl-β-carboline-3-carboxylic acid-(1-methyl-2-methoxy)-ethyl ester, melting point 123°–125° C.

6-Benzyloxy-4-methoxymethyl-β-carboline-3-carboxylic acid-(1-methyl-2-benzyloxy)-ethyl ester, melting point 103°–105° C.

5-Isopropoxy-4-methyl-β-carboline-3-carboxylic acid-(2-methoxy)-ethyl ester, melting point 105°–106° C.

5-Isopropoxy-4-ethyl-β-carboline-3-carboxylic acid-(2-methoxy)-ethyl ester, melting point 103°–104° C.

5-Isopropoxy-4-ethyl-β-carboline-3-carboxylic acid-(2-hydroxy)-ethyl ester, melting point 104°–105° C.

5-Methoxy-4-ethyl-β-carboline-3-carboxylic acid-(2-hydroxy)-ethyl ester, melting point 85°–86° C.

2-Hydroxy-1-methylpropyl-6-benzyloxy-4-methoxymethyl-β-carboline-3-carboxylate, melting point 121°–126° C.

(1RS, 2SR-2-hydroxy-1-methylpropyl)-6-benzyloxy-4-methoxymethyl-β-carboline-3-carboxylate, melting point 91°–94° C.

EXAMPLE 6

135 mg of 6-benzyloxy-4-methoxymethyl-β-carboline-3carboxylic acid-(2-phenyl-1,3-dioxan-5-yl)-ester under 10 ml of acetone and 100 ml of 4N hydrochloric acid is stirred for 1 hour at 80° C. bath temperature. The batch is concentrated by evaporation, taken up in aqueous ammonia and suctioned off. 100 mg of 6-benzyloxy-4-methoxymethyl-β-carboline-3-carboxylic acid-(1,3-dihydroxy-propan-2-yl)-ester of a melting point of 190°–192° C. is obtained.

Analogously 6-benzyloxy-4-methoxymethyl-β-carboline-3-carboxylic acid-(2,3-dihydroxy-prop-1-yl)-ester of a melting point of 190°–192° C. is produced from 6-benzyloxy-4-methoxymethyl-β-carboline-3-carboxylic acid-(2,2-dimethyl-1,3-dioxolan-4-yl)-methyl ester at room temperature.

We claim:
1. Compounds of formula I

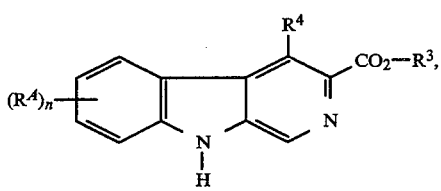

in which
$R^A$ is halogen, —$CHR^1$—$R^2$ or —$OR^5$, and
n is 1 or 2,
wherein
$R^1$ is hydrogen or $C_{1-4}$-alkyl,
$R^2$ is hydrogen, $C_{1-4}$-alkyl, O-$C_{1-4}$-alkyl or a phenyl, benzyl or phenoxy radical, optionally substituted 1 to 3 times by halogen, nitro, cyano, $C_{1-4}$-alkyl, $C_{1-4}$-alkoxy, trifluoromethyl, -$SO_2$-$C_{1-4}$-alkyl, amino and $C_{1-4}$-alkoxycarbonyl group(s),
$R^5$ is hydrogen, $C_{1-4}$-alkyl, $C_{3-7}$-cycloalkyl or a phenyl, benzyl or hetaryl radical optionally substituted 1 to 3 times by halogen, nitro, cyano, $C_{1-4}$-alkyl, $C_{1-4}$-alkoxy, trifluoromethyl, -$SO_2$-$C_{1-4}$-alkyl, amion and $C_{1-4}$-alkoxycarbonyl group(s), wherein the hetaryl radical is a pyridine, pyrimidine, pyrazine, pyridazine, triazine, furan, thiophene, pyrrole, thiazole, imidazole, quinoline, isoquinoline or quinoxaline radical,
$R^4$ is hydrogen, $C_{1-4}$-alkyl or $C_{1-4}$-alkoxy-$C_{1-2}$-alkyl, and
$R^3$ is a straight-chain or branched $C_{1-6}$-alkyl, that is substituted one to four times with $OR^6$,
wherein
$R^6$ is hydrogen, $C_{1-4}$-alkyl or a hydroxy protective group, or isomers or pharmaceutically acceptable acid addition salts thereof.

2. 6-Benzyloxy-4-methoxymethyl-β-carboline-3-carboxylic acid-(2-hydroxy-2-methyl)-propyl ester
6-hydroxy-4-methoxymethyl-β-carboline-3-carboxylic acid-(2-hydroxy-2-methyl)-propyl ester
4-methoxymethyl-6-(2-pyrazinyloxy)-β-carboline-3-carboxylic acid-(2-hydroxy-2-methyl)-propyl ester
6-(5-bromo-2-pyridyloxy)-4-methoxymethyl-β-carboline-3-carboxylic acid-(2-hydroxy-2-methyl)-propyl ester.

3. A pharmaceutical agent comprising an effective amount for soporific, anxiolytic or memory-promoting activity of at least one of the compounds of claim 1 and a pharmaceutically acceptable vehicle.

4. A pharmaceutical agent comprising an effective amount for soporific, anxiolytic or memory-promoting activity of at least one of the compounds of claim 2 and a pharmaceutically acceptable vehicle.

5. The compound of claim 1, wherein at least one $OR^6$ is a hydroxy protective group selected from the group consisting of cyclic ether, benzyl, substituted benzyl, trityl, allyl and trialkylsilyl radicals or, where at least two $OR^6$ groups are present together forming a hydroxy protective group selected from the group consisting of cyclic acetal and cyclic ketal radicals.

6. The compound of claim 5, wherein the hydroxy protective group(s) are selected from the group consisting of tetrahydropyranyl, tetrahydrofuranyl, benzyl, p-methoxybenzyl, 4-methylbenzyl, trityl, allyl, trimethylsilyl, t-butyldimethylsilyl, 1,3-dioxane, 1,3-dioxolane, 2-phenyl-1,3-dioxane, and 2,2-dimethyl-1,3-dioxolane radicals.

* * * * *